United States Patent [19]

Birk et al.

[11] 4,327,724

[45] May 4, 1982

[54] PNEUMATICALLY OPERABLE INJECTION DEVICE

[76] Inventors: Michael Birk, Liebigstrasse 5, 8000 München 22; Ullrich Pfeiffer, Walserstrasse 8, 8000 München 80, both of Fed. Rep. of Germany

[21] Appl. No.: 154,582

[22] Filed: May 29, 1980

[30] Foreign Application Priority Data

May 30, 1979 [DE] Fed. Rep. of Germany ....... 2922037

[51] Int. Cl.³ .............................................. A61M 5/00
[52] U.S. Cl. .............................................. 128/218 A
[58] Field of Search ........ 128/218 A, DIG. 1, 214 E, 128/224, DIG. 12, DIG. 13

[56] References Cited

U.S. PATENT DOCUMENTS

| | | | |
|---|---|---|---|
| 3,768,472 | 10/1973 | Hodosh et al. | 128/218 A |
| 4,108,176 | 8/1978 | Walden | 128/218 A |
| 4,212,298 | 7/1980 | Gezari | 128/218 A |

*Primary Examiner*—John D. Yasko
*Attorney, Agent, or Firm*—Fleit & Jacobson

[57] ABSTRACT

A pneumatically operable injection device has a first pressure cylinder with a piston which is adapted to be rigidly but detachably connected to a piston of an injection syringe, and a second pressure cylinder with a piston having an extension adapted to co-operate with a three-way cock in such a manner as to cause the three-way cock to be operated by movement of its piston. Flow connections are provided between the outlet of the injection syringe and the three-way cock, between the three-way cock and a connecting piece, and between the three-way cock and an inlet of a reservoir for the substance to be injected. The device is adapted to effect either a connection between the outlet of the injection syringe and the connecting piece or between the syringe outlet and the reservoir. Compressed-air lines are provided for the purpose of pneumatically operating the pistons in the two pressure cylinders. Bleed valves disposed in the compressed-air lines are adapted to be controlled electronically in such a manner that the pneumatically effected filling step can only be initiated with the three-way cock being in the position in which it connects the syringe outlet with the reservoir and that a subsequent injection step can only be effected with the three-way cock in a position in which it connects the syringe outlet with the connecting piece.

7 Claims, 3 Drawing Figures

PNEUMATICALLY OPERABLE INJECTION DEVICE

FIELD OF THE INVENTION

The present invention relates to a pneumatically operable injecting device which is adapted to inject liquids into a living organism with the injecting step resembling a pulse.

DESCRIPTION OF THE PRIOR ART

In the field of measuring flow rates, there has been known the indicator diluting method suggested by Stewart Hamilton; where this method is employed, an indicator such as a dye, isotopes or a cold, physiologically harmless solution is injected into a blood vessel and the concentration or the change in temperature downstream of the injection site is detected; this method has proved particularly useful for the determination of the volumetric cardiac output; in recent years, this method has been adopted to an ever increasing extent. More in particular, this includes the known thermodilution method in which use is made of an indicator in the form of a refrigerated, physiologically harmless solution which is injected into a blood vessel, with the change in temperature downstream of the injection site being detected, it thus being possible, for the purpose of measuring the volumetric cardiac output, for example to calculate the desired output values on the basis of such changes in temperature (see The American Journal of Cardiology, Vol. 29, February 1972, pages 241 to 246). For the purpose of recording and interpreting such measured values with the object of determining the cardiac output, use may be made of so-called heart volume computers which are available, for example, from Edwards Laboratories, Santa Ana, U.S.A.

A major problem associated with the above-described indicator diluting method resides in the fact that it is necessary that the entire indicator volume be introduced into the blood vessel at the injection site with practically no delay at all so as to permit the attainment of measured values downstream of the injection site which are as accurate as possible and which are reproducible; of course, there exist physiological and technical limitations which render it difficult to reach such ideal conditions; it is generally desired to inject an indicator volume of 10 milliliters, for example, within a prescribed period of time; in the case of manual injection, such a quantity can be injected within approximately 3 sec, but it requires a considerable amount of skill on the part of a person performing the injection step. Another source of inaccuracies of the measured values which are obtained with manual injection of an indicator resides in the fact that different persons are likely to inject the indicator at different rates and that even one and the same person may not be expected to attain uniform injection periods.

Thus far the above-mentioned drawbacks have been taken into account by the development of automatic injection devices in which the injection piston is operated pneumatically, the rate of injection amounting to between 2.0 and 4.0 milliliters/sec.

Investigations have shown that optimum conditions of mixing the indicator and the blood will be obtained if the rate of injection based on the same cross-section of the flow equals approximately 15 times the blood flow rate, this being so because such an injection rate will not yet give rise to any physiological damage such as, for example, destruction of blood corpuscles.

The injection rates attainable by a skilled physician employing the manual injection method or using the aforedescribed injection device correspond to approximately 7 times the rate of blood flow.

OBJECT OF THE INVENTION

In view of the above, it is an object of the present invention to provide an injection device in which the rate of injection is continuously variable so as to permit an optimum injection rate to be obtained.

It is another object of the present invention to provide an injection device which is constructed in such a manner that, where the thermal dilution method is employed, it is not necessary to transfer the injection syringe from a cooling bath into the injection device, it being understood that under normal conditions such a transfer is liable to result in the syringe being heated so that the inaccuracy of the measured values will be increased. In cases in which, for the purpose of determining the volume of the heart by means of the thermal dilution method in connection with a cardiac output computer, the computer, after having been made ready for receiving the measured values, will produce a signal, preferably an acoustic signal, whereupon the physician will initiate injection; this procedure is liable to result in undesirable delays; it is another object of the present invention to prevent the occurrence of such delays. In order to make it possible, as compared with conventional injection methods, to obtain a considerably larger number of measured values per unit time, e.g. in the case of high-risk patients, where the employment of a continuous measuring method is desired, the device of the present invention should be constructed to meet these requirements.

SUMMARY OF THE INVENTION

The said objects of the invention are attained by the provision of an injection device constructed in the manner shown in the main claim and of modifications thereof described in the sub-claims. The injection device of the present invention is adapted to avoid the drawbacks of the hitherto known injection devices and to provide highly accurate and reproducible measured values, thus enabling improved results in conjunction with the employment of smaller indicator quantities.

BRIEF EXPLANATION OF THE DRAWINGS

The invention may be carried into practice in a number of ways but a specific embodiment will now be described by way of example with reference to the accompanying drawings, in which.

DETAILED DESCRIPTION OF THE PREFERRED EMBODIMENT

Figure 1:
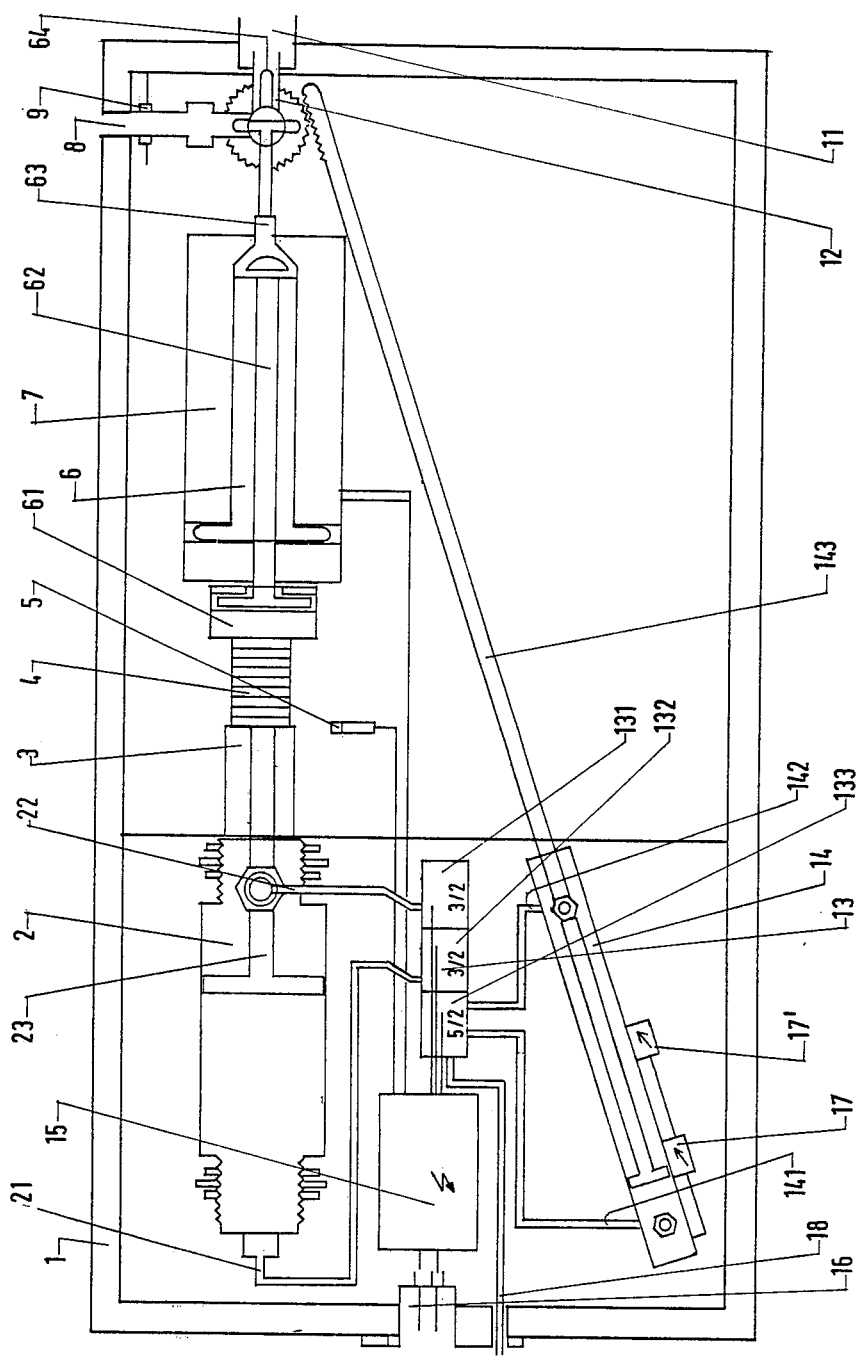
FIG. 1 is a front view of an injection device of the invention.

According to FIG. 1, the illustrated device comprises a housing 1 accommodating in its rear section a pneumatic cylinder 2 having a pneumatic line 21 connected to its rear end and another pneumatic line 22 connected to its front end; in said pneumatic cylinder, a piston 23 is slidably supported. An hydraulic piston damping means 3 is provided for the purpose of adjusting a slow rate of piston retraction. Reference numeral 4 designates a piston stroke determining means mounted on a piston rod 23 of cylinder 2 and adapted to co-operate with a piston stroke measuring means 5 (explained further below) for the purpose of continuously varying the length of the piston stroke, said piston stroke measuring means being controlled electronically in a per se known manner. The injection syringe 6 is of a standard commercial single-use type. For the purpose of transmitting pulling and pushing forces exerted by piston 23 on the piston 62 of syringe 6, there is provided a piston guide member 61 which serves to connect together the two pistons and which is adapted to be detachably locked to the handle of injection piston 62. Syringe 6 is disposed in a cooling block 7 which is adapted in a per se known manner thermostatically to control the temperature of the contents of syringe 6. The outlet 63 of syringe 6 is connected to a three-way cock 12 which is adapted either to effect a connection to an adaptor 64 or to effect a connection to a reservoir 8 containing the substance to be injected.

The flow line leading to reservoir 8 is provided with a flow meter 9 designed to monitor the substance to be injected for freedom from air bubbles, said flow meter being preferably constructed as an electronic flow meter (e.g. as a capacitive meter and preferably measuring a resistance) and serving to prevent air bubbles from entering into syringe 6 during filling thereof from reservoir 8.

Three-way cock 12 is rigidly attachable to a gear wheel which may be rotated for the purpose of adjusting the cock. Another piston rod 143 shown in FIG. 1 is formed as a rack section at its end which is adjacent to said gear wheel, said rack section meshing with the gear wheel of three-way cock 12. Piston rod 143 which co-operates with another pneumatic cylinder 14 permits three-way cock 12 to be adjusted by moving the piston rod in a forward or backward direction. The ends of cylinder 14 are connected to a compressed-air line 141 and 142, respectively. Syringe 6, three-way cock 12, the lines leading to reservoir 8 for the substance to be injected as well as the connections between these elements and those leading to a catheter are all commercial items; all connections are preferably of the Luer Look type which is a connector of special design.

The respective other ends of pneumatic lines 21 and 22 are each provided with an electromagnetically pilot-controlled pneumatic 3/2-way valve 131 and 132, respectively; the pneumatic lines 141 and 142 are provided, at their other ends, with a common 5/2-way valve; these valves serve to control, within the system shown, the flow of compressed air coming from a supply line 18.

The stroke length of cylinder 14 is limited by merely mechanical means. The limit switches 17 and 17' serve to indicate the momentary position of the piston, that is to say they permit checking whether or not the three-way cock is in its correct position for the subsequent step to be performed (filling of syringe or injection). Control of valve 13, of the length of piston stroke via control means 4 and piston stroke measuring means 5 in accordance with the required injection volume and thus the control of the quantity to be injected and the duration of the injection step as well as the position of three-way cock 12 is effected electronically in a per se known manner. Also connected to these control means is flow meter 9 for excluding air bubbles from the substance to be injected, the connection being such that upon air bubbles passing the flow meter, for example upon reservoir 8 becoming empty, refilling of syringe 6 will be interrupted.

If desired, the injection device may be provided, at its electronic control section, with an input 16 with which a measuring instrument, e.g. a cardiac output computer, may call for an injection unless the injection starting signal is inputted manually by depression of a key. In cases in which the injection device is not ready for operation or if some breakdown has occurred, this signal will be suppressed.

In order further to facilitate the understanding of the inventive device, a complete filling and injection cycle will now be described.

With the device at rest, operating piston 23 is not subjected to pressure, i.e. valves 131 and 132 are de-energized. Piston rod 23 is in its extended position, making it possible to insert an empty syringe 6 into the cooling block 7 and to engage the handle of the syringe piston into guiding or holding means 61. With the device in this rest position, three-way cock 12 is in such a position that syringe 6 is connected to reservoir 8.

Filling of syringe 6 may be initiated either by means of a cardiac output computer if the computer has a suitable output and by way of the electronic control section or manually by depression of a key. Limit switch 17 makes a check as to whether or not three-way cock 12 keeps reservoir 8 connected to syringe 6. If this connection has been established, 3/2-way valve 131 is energized so as to cause piston 23 to be subjected to pressure in its pulling direction. The filling step is terminated, i.e. valve 131 is de-energized, as soon as syringe 6 has received the preset quantity of the substance to be injected. The volume of the quantity of the substance to be injected is measured by means of piston stroke adjuster 4 and piston stroke measuring means 5.

Piston stroke measuring means 5 is an optoelectronic component containing an infrared transmitter and an infrared receiver. As a measuring unit, piston stroke measuring means 5 reacts to variations in the reflective properties of piston stroke adjuster 4, which is provided with very poorly reflecting indicia, the space between any two adjacent indicia corresponding to a filling quantity of 1 milliliter. The electronic control unit counts the number of 1-milliliter indicia which have moved therepast and compares the count with the preset desired volume, the arrangement being such that the filling step is terminated upon the desired quantity of the substance to be injected being read. In the same manner as during initiation of the filling step, the injection step may also be initiated either by an external computer or manually by depression of a key. With three-way cock 12 in its "filling" position, 5/2-way valve 133 is energized, this resulting in piston rod 143 being extended by piston 14; piston rod 143 meshing with the gear wheel on three-way cock 12 moves the cock into its "injection" position. This position of the cock is signalled by the second limit switch 17' to the electronic control system which now energizes 3/2-way valve 132, thus causing operating cylinder 2 to be subjected to pressure in its pushing direction. This causes the substance to be injected to be forced out of the syringe and into the catheter. After a predetermined period of time has elapsed, a timing circuit again de-energizes the two valves 132 and 133 in order to return three-way cock 12 to its "filling" position and to unload operating system 2. The injection device is now again in its position of rest.

Figure 2:
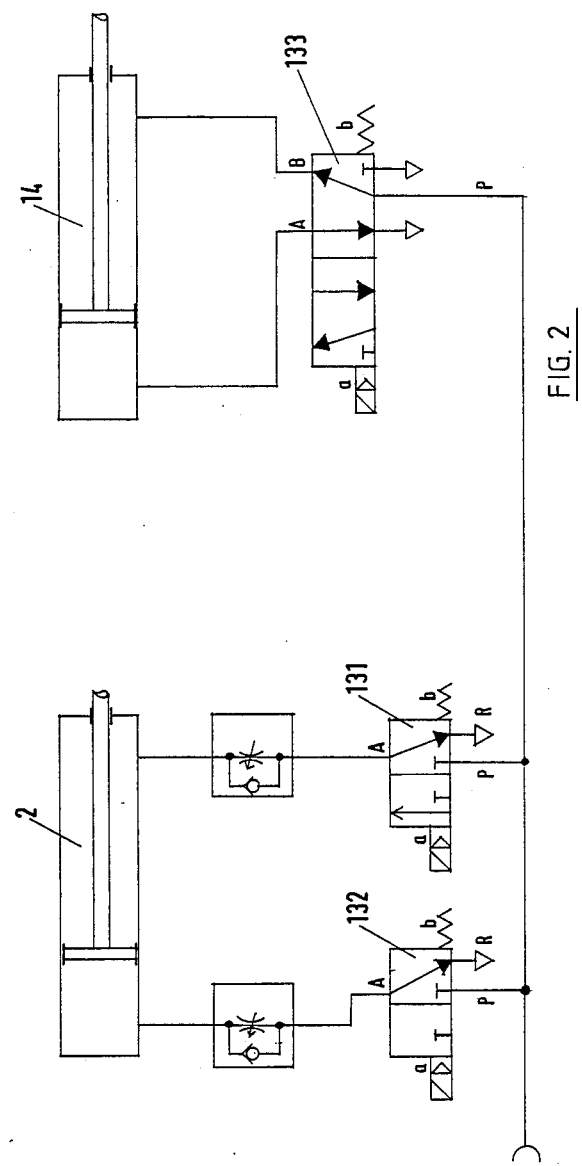
FIG. 2 is a diagram illustrating the inoperative positions of a plurality of valves of the injection device after filling of an injection syringe.

Should some mechanical defect render operation of three-way cock 12 impossible, the second limit switch 17' cannot send a signal to the electronic control system, the result being that no injection is performed and that the injection device is returned to its position of rest after a certain length of time. Should an injection device which is not ready for operation be called upon to perform an injection, it being understood that the syringe has not been filled, this will not harm the patient in any way whatever because no injection is carried out, this only being accompanied by the production of a useless measured value by the cardiac output computer. FIG. 2 diagrammatically indicates the positions of valves 133, 132 and 131 of the pneumatic system in the rest position of the injection device after syringe 6 has been filled. The letter "P" represents system pressure, the letter "R" represents pressure relief or air extraction, and the letter "A" represents a work junction.

What is claimed is:

1. A pneumatically operable injection device, characterized by a first pressure cylinder comprising a piston which is adapted to be rigidly but detachably connected to a piston of an injection syringe, a second pressure cylinder comprising a piston having an extension adapted to co-operate with a three-way cock in such a manner as to cause said three-way cock to be operated by movement of said piston, a flow connection between the outlet of said injection syringe and said three-way cock, a flow connection between said three-way cock and a connecting piece, a flow connection leading to an inlet of a reservoir for the substance to be injected, the device being adapted to effect either a connection between the outlet of the injection syringe and said connecting piece or between the syringe outlet and the connection of said reservoir, compressed-air lines provided for the purpose of pneumatically operating said pistons in said two pressure cylinders and bleed valves disposed in said compressed-air lines and adapted to be controlled electronically in such a manner that the pneumatically effected filling step can only be initiated with said three-way cock being in the position in which it connects the syringe outlet with the reservoir and that a subsequent injection step can only be effected with said three-way cock in a position in which it connects the syringe outlet with said connecting piece.

2. The injection device of claim 1, characterized by an opto-electronic component, preferably an infrared transmitter combined with an infrared receiver for use as a piston stroke measuring means adapted to co-operate with a piston stroke sensor mounted on an extension of the piston rod of said first pressure cylinder.

3. The injection device of claim 2, characterized in that said piston stroke sensor is provided on said extension of the piston rod of the first pressure cylinder in the form of poorly reflective indicia separated by calibrated spaces, the arrangement being such that detecting said indicia by means of said piston stroke measuring means and transferring corresponding signals to the electronic control section enables predetermined filling and injection quantities to be selected.

4. The injection device of any of the preceding claims, characterized by a flow meter adapted to monitor the substance to be injected for the absence of air bubbles in the flow line leading to said reservoir, said flow meter being preferably adapted to measure the flow electrically.

5. The injection device of claim 1 characterized by two limit switches associated with said second pressure cylinder and adapted to co-operate with the piston thereof in such a manner that one of said limit switches signals one operative position of said three-way cock and the other limit switch signals another operative position of said three-way cock, said signals being transmitted to said electronic control section.

6. The injection device of claim 1 characterized in that said injection syringe and said three-way cock are sterile expendable products.

7. The injection device of claim 1 characterized in that said expendable injection syringe is surrounded by an easily accessible cooling block which is adapted to be cooled, with the cooling being preferably controlled electrically in accordance with the Peltier cooling method.

* * * * *